United States Patent [19]

Boyd et al.

[11] Patent Number: 5,621,113
[45] Date of Patent: Apr. 15, 1997

[54] 4-[(THIEN-2-YL)METHYL]-IMIDAZOLE ANALGESICS

[75] Inventors: Robert E. Boyd, Horsham; Chris R. Rasmussen, Lansdale, both of Pa.; Jeffrey B. Press, Brewster, N.Y.

[73] Assignee: Ortho Pharmaceutical Corporation, Raritan, N.J.

[21] Appl. No.: 625,447

[22] Filed: Mar. 28, 1996

[51] Int. Cl.$^6$ .................................................. C07D 411/06
[52] U.S. Cl. ................................................................ 548/315.1
[58] Field of Search ............................................ 548/315.1

[56] References Cited

PUBLICATIONS

Kihara et al, "Preparation of imidazole derivatives, etc" CA112:139033 (1990).

*Primary Examiner*—Patricia L. Morris
*Attorney, Agent, or Firm*—John W. Harbour

[57] ABSTRACT

The 4-[(thien-2-yl)methyl]-imidazoles of the formulae:

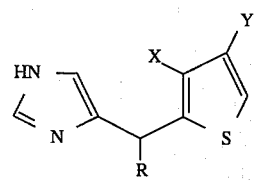

wherein
  R is hydrogen or methyl,
  X is hydrogen, $C_{1-4}$alkyl, bromine or chlorine, and
  Y is hydrogen, $C_{1-4}$alkyl, bromine or chlorine;
with the proviso that X and Y are not both simultaneously hydrogen.
have exceptional analgesic activity.

2 Claims, No Drawings

4-[(THIEN-2-YL)METHYL]-IMIDAZOLE ANALGESICS

The present invention relates to $\alpha_2$-adrenoceptor agonists having analgesic activity. More particularly, the present invention relates to 4-[(thien-2-yl)methyl]-imidazoles having improved analgesic activity.

BACKGROUND OF THE INVENTION

Clonidine is a centrally acting $\alpha_2$-adrenoceptor agonist with wide clinical utility as an antihypertensive agent. Clonidine is believed to act by inhibiting the release of norepinephrine from sympathetic nerve terminals via a negative feedback mechanism involving $\alpha_2$-adrenoceptors located on the presynaptic nerve terminal. This action is believed to occur in both the central (CNS) and peripheral (PNS) nervous systems. More recently, the role of $\alpha_2$-adrenoceptor agonists as analgesic agents in humans and antinociceptive agents in animals has been demonstrated. Clonidine and other $\alpha_2$-adrenoceptor agonists have been shown to produce analgesia through a non-opiate mechanism and, thus, without opiate liability. However, other behavioral and physiological effects were also produced, including sedation and cardiovascular effects.

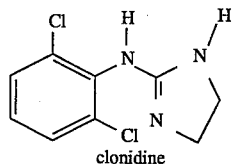
clonidine

Medetomidine and detomidine are $\alpha_2$-adrenoceptor agonists widely used clinically in veterinary medicine as sedatives/hypnotics for pre-anaesthesia. These compounds are hypotensive in animals and in humans, but the magnitude of this cardiovascular effect is relatively insignificant.

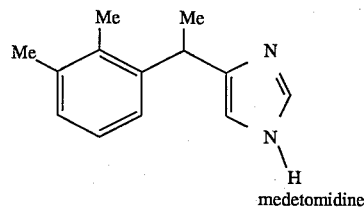
medetomidine

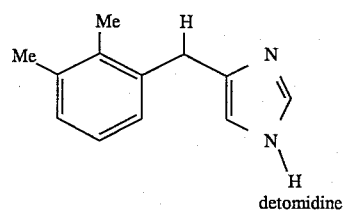
detomidine

U.S. Pat. No. 3,574,844, Gardocki et al., teach 4-[4(or 5)-imidazolylmethyl]-oxazoles as effective analgesics. The disclosed compounds are of the general formula:

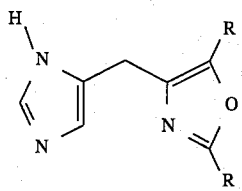

Compounds of this type are insufficiently active and suffer from unwanted side effects.

U.S. Pat. No. 4,913,207, Nagel et al., teach arylthiazolylimidazoles as effective analgesics. The disclosed compounds are of the general formula:

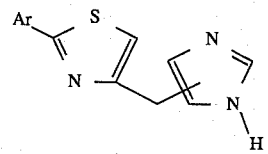

Compounds of this type are insufficiently active and suffer from unwanted side effects.

WO92/14453, Campbell et al., teach 4-[(aryl or heteroaryl)methyl]-imidazoles as effective analgesics. The disclosed compounds are of the general formula:

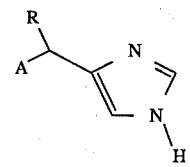

The disclosed compounds are insufficiently active and suffer from unwanted side effects.

Kokai No. 1-242571, Kihara et al., disclose a method to produce imidazole derivatives for use, among other uses, as antihypertensive agents.

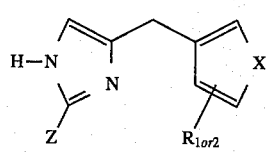

A single mixture of compounds meeting the above formula was reportedly produced by the inventive method. This was a mixture of 4-(2-thienyl)-methylimidazole and 4-(3-thienyl)-methylimidazole represented by the following formula:

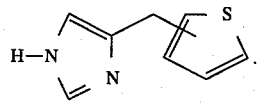

The disclosed compounds are insufficiently active and suffer from unwanted side effects.

It is an object of the present invention to produce 4-[(thien-2-yl)methyl]-imidazoles having improved analgesic activity.

It is another object of the present invention to produce 4-[(thien-2-yl)methyl]-imidazole analgesics having reduced side effects.

SUMMARY OF THE INVENTION

Briefly, there is provided by the present invention compounds having improved analgesic activity of the formula:

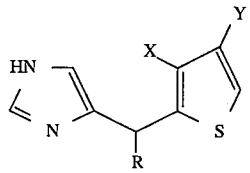

wherein
R is hydrogen or methyl,
X is hydrogen, $C_{1-4}$ alkyl, bromine or chlorine, and
Y is hydrogen, $C_{1-4}$ alkyl, bromine or chlorine;
with the proviso that X and Y are not both simultaneously hydrogen.

DETAILED DESCRIPTION OF THE INVENTION

The compounds of the present invention may be made in basically a two step process. In the first step, an appropriately substituted precursor thiophene is obtained having hydrogen, $C_{1-4}$ alkyl, bromine or chlorine substituents as desired and in the required positions. This precursor thiophene will have an electrophilic carbon substituent at the 2-position. In the second step, a precursor imidazole having an anion at the 4-position capable of reacting with the electrophilic carbon of the precursor thiophene to leave a carbon bridge residue, is reacted with the precursor thiophene to produce the target skeleton followed by deoxygenation of the bridge residue. Of course, many variations are possible. It may be desirable to substitute the thiophene initially, as described, or to modify the substitution on the thiophene following the formation of the base structure of the final compound. Also, in compounds where it is desirable to have methyl substitution on the carbon bridge residue, additional steps will be necessary.

Herein, a Grignard reaction is favored for use in the second step to join the thienyl moiety and the imidazolyl moiety. Thus, it is preferred that the precursor imidazole be substituted at the 4-position as a Grignard reagent and that the precursor thiophene is substituted at the 2-position with a carbonyl, such as, formyl or N,O-dimethylcarboxamido group.

The preferred precursor imidazole has the formula:

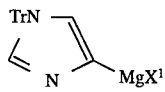

where $X^1$ is iodo, bromo or chloro. This compound may be made by methods well known to the art, i.e., reaction between alkyl Grignard or magnesium and imidazolyl halide in dry, alcohol-free ether or THF or dichloromethane.

The preferred precursor thiophenes have the formula:

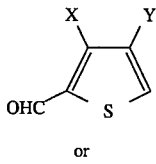

or

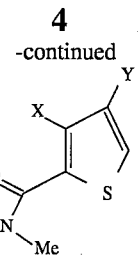

where X and Y are defined above. As starting materials to make the preferred precursor thiophenes AA and BB, the preparation of various brominated and methylated thiophenes is well known from the literature. Precursor thiophenes of type AA may be produced from 3,4-disubstituted thiophenes or 3-substituted thiophenes by use of a Vilsmeier formylation. The Vilsmeier formylation is carried out by simply heating the substituted thiophene in DMF and $POCl_3$. The resultant compound is 3-substituted-thiophene-2-carboxaldehyde or 4-substituted-thiophene-2-carboxaldehyde or 3,4-disubstituted-thiophene-2-carboxaldehyde. Where the starting material is a 3-substituted thiophene, these resultant compounds may be produced in some cases as mixtures of thiophene-(2 and 5)-carboxaldehydes. Of course, the 3-substituted-thiophene-5-carboxaldehydes are the 4-substituted-thiophene-2-carboxaldehydes. In the case of a mixture, the desired pure compound may be recovered by standard techniques, including chromatography and recrystallization. Alternatively, certain precursor thiophenes of type AA may be produced from 2-bromo-3,4-disubstituted-thiophenes or 2-bromo-3-substituted-thiophenes or 2-bromo-4-substituted-thiophenes by use of halogen metal exchange. In a first step, the compound is treated with an organo-alkali compound such as n-butyllithium, the product of which is reacted, in a second step, in situ with DMF. The reaction is quenched with aqueous ammonium chloride. The resultant compound is 2-carboxaldehyde-3,4-didisubstituted-thiophene or 2-carboxaldehyde-3-substituted-thiophene or 2-carboxaldehyde-3-substituted-thiophene.

Precursor thiophenes of type BB may be produced from 3-(methyl or chloro or bromo)-4-(methyl or chloro or bromo)-thiophene-2-carboxylate or 3-(methyl or chloro or bromo)-thiophene-2-carboxylate or 4-(methyl or chloro or bromo)-thiophene-2-carboxylate by two methods. In the first method, the carboxylate starting material is converted to the acid chloride and reacted with N,O-dimethylhydroxylamine to produce the Weinreb amide, thiophene type BB. In the second method, the carboxylate is reacted with N,O-dimethylhydroxylamine and an appropriate coupling agent, such as, DCC or CDI, to produce the Weinreb amide.

The precursor imidazole may be reacted with any of the precursor thiophenes of types AA or BB by use of the Grignard Reaction. Where the precursor thiophene is of type AA, a solution of the thiophene precursor is combined with a solution of the imidazole precursor at room temperature and the reaction is quenched with aqueous ammonium chloride solution to produce an imidazo thienyl methanol. The carbinol is deoxygenated to final product, where R is hydrogen, by use of a reducing agent, such as borane methyl sulfide in combination with TFA. Alternatively, the methanol is catalytically deoxygenated to final product, where R is hydrogen, by heating with Pearlman's catalyst and an equivalent of acid. To produce final product where R is methyl, the methanol is oxidized to the corresponding ketone with an oxidizing agent, such as $MnO_2$ or Jones Reagent and the resulting ketone is reacted with methyl Grignard to produce a carbinol which is deoxygenated as described immediately above. Where the precursor thiophene is of type BB, a solution of the thiophene precursor is combined with a solution of the imidazole precursor at room temperature and the reaction is quenched with aqueous ammonium chloride solution to produce an imidazo thienyl ketone. To produce final product on which R is hydrogen, the ketone is reduced to the carbinol by use of a reducing agent, such as, sodium borohydride or lithium aluminum hydride and thereafter the carbinol is deoxygenated as described immediately above. Alternatively, to produce final product on which R is methyl, the imidazo thienyl ketone is reacted with methyl Grignard to produce a carbinol which is deoxygenated as described above.

The protecting group on the precursor imidazole is exemplified herein as trityl, which is preferred. However, a person skilled in the art will readily recognize that other protecting groups are suitable. Suitable protecting groups include dimethylsulfamoyl or methoxymethyl. The trityl group is removed in the deoxygenation to final product or upon heating in a dilute acid and alcoholic solvent.

The most preferred compounds of the instant invention are shown in Table I:

TABLE I

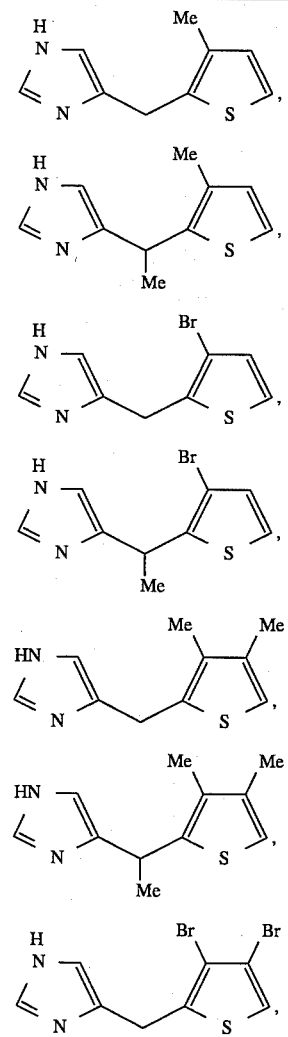

TABLE I-continued

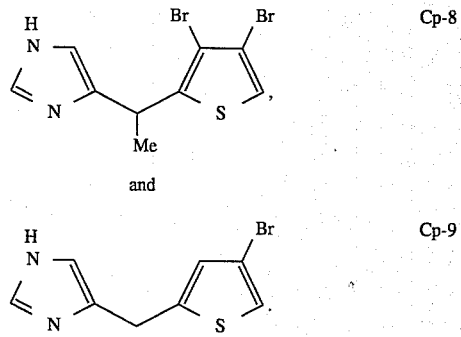

The activity of compounds of the invention as analgesics may be demonstrated by the in vivo and in vitro assays as described below:

Alpha$_{2D}$ adrenergic receptor binding assay

Male, Wistar rats (150–250 g, VAF, Charles River, Kingston, N.Y.) are sacrificed by cervical dislocation and their brains removed and placed immediately in ice cold HEPES buffered sucrose. The cortex is dissected out and homogenized in 20 volumes of HEPES sucrose in a Teflon®-glass homogenizer. The homogenate is centrifuged at 1000 g for 10 min, and the resulting supernatant centrifuged at 42,000 g for 10 min. The resulting pellet is resuspended in 30 volumes of 3 mM potassium phosphate buffer, pH 7.5, preincubated at 25° C. for 30 min and recentrifuged. The resulting pellet is resuspended as described above and used for the receptor binding assay. Incubation is performed in test tubes containing phosphate buffer, 2.5 mM MgCl$_2$, aliquots of the synaptic membrane fraction, the ligand $^3$H-para-aminoclonidine and test drug at 25° C. for 20 min. The incubation is terminated by filtration of the tube contents through glass fiber filter sheets. Following washing of the sheets with 10 mM HEPES buffer, the adhering radioactivity is quantified by liquid scintillation spectrometry.

Binding of the test drug to the receptor is determined by comparing the amount of radiolabeled ligand bound in control tubes without drug to the amount of radiolabeled ligand bound in the presence of the drug. Dose-response data are analyzed with LIGAND, a nonlinear curve fitting program designed specifically for the analysis of ligand binding data. This assay is described by Simmons, R. M. A., and Jones, D. J., Binding of [$^3$H-]prazosin and [$^3$H-]p-aminoclonidine to α-Adrenoceptors in Rat Spinal Cord, Brain Research 445:338–349, 1988.

Mouse Acetylcholine Bromide-Induced Abdominal Constriction Assay

The mouse acetylcholine bromide-induced abdominal constriction assay, as described by Collier et al. in Brit. J. Pharmacol. Chem. Ther., 32: 295–310, 1968, with minor modifications was used to assess analgesic potency of the compounds herein. The test drugs or appropriate vehicle were administered orally (p.o.) and 30 minutes later the animal received an intraperitoneal (i.p.) injection of 5.5 mg/kg acetylcholine bromide (Matheson, Coleman and Bell, East Rutherford, N.J.). The mice were then placed in groups of three into glass bell jars and observed for a ten minute observation period for the occurrence of an abdominal constriction response (defined as a wave of constriction and elongation passing caudally along the abdominal wall, accompanied by a twisting of the trunk and followed by extension of the hind limbs). The percent inhibition of this response to a nociceptive stimulus (equated to % analgesia) was calculated as follows: The % Inhibition of response, i.e., % analgesia is equal to the difference between the number of control animals response and the number of drug-treated animals response times 100 divided by the number of control animals responding.

At least 15 animals were used for control and in each of the drug treated groups. At least three doses were used to determine each dose response curve and $ED_{50}$ (that dose which would produce 50% analgesia). The $ED_{50}$ values and their 95% fiducial limits were determined by a computer assisted probit analysis.

of the invention will vary as will the pain being treated. Pharmaceutical compositions of the invention comprise the formula (I) compounds as defined above, particularly in admixture with a pharmaceutically-acceptable carrier.

To prepare the pharmaceutical compositions of this invention, one or more compounds of the invention or salt thereof as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers

TABLE II

| | | Mouse Abdominal Constriction | |
|---|---|---|---|
| Compound | Ki(nm) | % Inhibition | $ED_{50}$ |
| Cp-1 | 0.45 | | 0.94 mpk/po |
| Cp-2 | 2.1 | | 1.4 mpk/po |
| Cp-3 | 0.35 | | 1.7 mpk/po |
| Cp-4 | 0.96 | | 2.1 mpk/po |
| Cp-5 | 0.17 | 100% @ 30 mpk/po | |
| Cp-6 | 0.75 | 87% @ 30 mpk/po | |
| Cp-7 | 0.43 | 80% @ 30 mpk/po | |
| Cp-8 | 0.07 | | 5.7 mpk/po |
| Cp-9 | 1.4 | 80% @ 30 mpk/po | |
| [structure: HN-pyrimidine-CH2-thiophene-Me] | 3.6 | 33% @ 30 mpk | |
| [structure: HN-pyrimidine-CH2-thiophene] | 8.7 | 60% @ 30 mpk | |
| [structure: HN-pyrimidine-CH(Et)-thiophene-Me] | 8.3 | 100% @ 30 mpk | |
| [structure: HN-pyrimidine-C(=CMe2)-thiophene-Me] | 335 | 47% @ 30 mpk | |
| [structure: HN-pyrimidine-C(=CMe2)-thiophene-Me] | 1000 | 73% @ 30 mpk | |

Based on the above results, invention compounds of the present invention may be used to treat mild to moderately severe pain in warm-blooded animals, such as, humans by administration of an analgesically effective dose. The dosage range would be from about 10 to 3000 mg, in particular about 25 to 1000 mg or about 100 to 500 mg, of active ingredient 1 to 4 times per day for an average (70 kg) human although it is apparent that activity of individual compounds and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above.

The pharmaceutically acceptable salts referred to above generally take a form in which the imidazolyl ring is protonated with an inorganic or organic acid. Representative organic or inorganic acids include hydrochloric, hydrobromic, hydroiodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic or saccharic.

The following Examples illustrate the invention:

EXAMPLE 1

4-[(3-Methylthien-2-yl)methyl]-1H-imidazole Hydrochloride step A

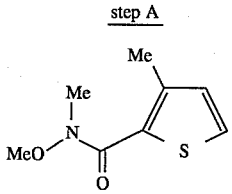

A1

Thionyl chloride (21.4 g, 0.18 mol) was added to a solution of 3-methylthiophene-2-carboxylic acid (21.3 g, 0.15 mol) in 100 mL of chloroform. The reaction mixture was refluxed for 2 h and then was allowed to cool. In a separate flask, a solution of N,O-dimethylhydroxylamine hydrochloride (21.9 g, 0.225 mol) in 300 mL of chloroform was cooled in ice. Then triethylamine (56 mL, 0.4 mol) was added followed by a solution of the 3-methylthiophene-2-carboxylic acid chloride. The reaction mixture was allowed to warm to ambient temperature and was stirred overnight. The reaction mixture was poured into a separatory funnel and washed with dilute aqueous hydrochloric acid and then with water. The organic layer was dried (MgSO$_4$) and concentrated to give a yellow oil. Distillation afforded 19.0 g (68%) of N,O-dimethyl-3-methylthiophene-2-carboxamide, A1, as a colorless liquid, bp 91°–93° C. (0.05 mmHg). The $^1$H NMR in CDCl$_3$ supported the assigned structure.

step B

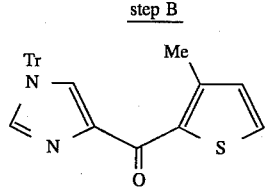

B1

To a solution of 4-iodo-1-trityl imidazole (32.7 g, 0.075 mol) in 300 mL of dry dichloromethane under nitrogen was added dropwise a solution of ethylmagnesium bromide (25.0 mL, 3.0M) in diethyl ether. When the addition was complete, the reaction mixture was stirred for 1 h at 25° C. TLC analysis indicated that the starting material was gone so N,O-dimethyl-3-methylthiophene-2-carboxamide, A1, (13.9 g, 0.075 mol) was added dropwise over 2 h as a solution in tetrahydrofuran. After overnight stirring at ambient temperature, the reaction was quenched with saturated ammonium chloride solution. The layers were separated, and the aqueous layer was extracted again with dichloromethane. The organic layers were combined, dried (Na$_2$SO$_4$), and concentrated. The residue was recrystallized from acetone to afford (3-methylthien-2-yl)-1-trityl-imidazol-4-yl methanone, B1, as a beige solid. The $^1$H NMR in CDCl$_3$ supported the assigned structure.

step C

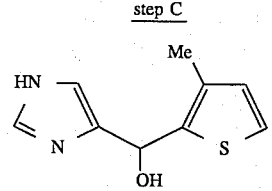

C1

A solution of (3-methylthien-2-yl)-imidazol-2-yl methanone (7.7 g, 0.018 mol) and sodium borohydride (1.03 g, 0.027 mol) in 50 mL of 2-propanol was heated at reflux for 2 hours. After cooling, 3N hydrochloric acid solution was added to the reaction mixture followed by 10% aqueous sodium carbonate solution. The mixture was concentrated under reduced pressure and the resulting solution was extracted twice with chloroform. Organic extracts were combined, dried (Na$_2$SO$_4$), and concentrated. The residue was recrystallized from ethyl acetate with a small amount of chloroform to give a white solid. The mother liquor was concentrated to give a second crop of the desired (3-methylthien-2-yl)-1-trityl-imidazol-4-yl-methanol. The total yield from both crops was 7.2 grams (92%). The $^1$H NMR in CDCl$_3$ supported the assigned structure.

step D

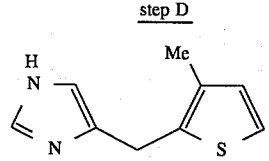

Cp-1

A solution of BH$_3$·THF (40 mL, 1.0M) in THF was added dropwise to a solution of TFA (9.1 g, 0.080 mol) in 20 mL of dry dichloromethane which was cooled in an ice bath. When the addition was complete, the alcohol, C1, (2.8 g, 0.0066 mol) was added in portions. The reaction mixture was stirred at 0° C. for 3 h. The reaction was quenched by careful addition of water, and the resulting mixture was basified with solid Na$_2$CO$_3$. This solution was extracted twice with dichloromethane. The organic extracts were combined and dried (K$_2$CO$_3$). A precipitate appeared to come out of solution which was filtered and the residue was washed with 10% methanoldichloromethane solution. The organic layers were combined and evaporated. The resulting residue was dissolved in methanol, and some insoluble material was removed by filtration. To this solution was added 10 mL of 3N HCl. This solution was stirred for 2 days. TLC analysis indicated some starting material was still present so the reaction mixture was heated to reflux. After 2 hours, the starting material was gone so the reaction mixture was cooled, and the solution was concentrated in vacuo. The residue was dissolved in water. This solution was washed twice with ether, basified with Na$_2$CO$_3$ and extracted with ethyl acetate. The ethyl acetate extracts were combined, dried ($Na_2SO_4$), and concentrated to give 1.1 g of an amber syrup. This material was passed through a flash silica gel column using 98:2 chloroform:10% ammonium hydroxide in methanol. The separation was very poor so the material was repurified on flash silica gel with 98:1:1 ethyl acetate::methanol:ammonium hydroxide as eluent. The product containing fractions were combined to give 0.25 g of material which was repurified on flash silica gel using 98:1:1 ethyl acetate:methanol:ammonium hydroxide. The product containing fractions were combined and concentrated. The residue was dissolved in ethyl acetate and heated with ethereal HCl. The solid which precipitated was collected and recrystallized from acetone with a drop of water. The collected solid was dried under vacuum to give 0.060 g of white needles, Cp-1, mp 127.5°–129° C. The $^1$H NMR in DMSO-$d_6$ supported the assigned structure: d2.15–2.25 (d, 3H, Me), 4.10–4.20 (s, 2H, $CH_2$), 6.85–6.95 (d, 1H), 7.30–7.40 (d, 1H), 7.40–7.50 (s, 1H), 8.95–9.05 (s 1H), 14.35–14.5 (br s, 2H). Elemental analysis: Calculated for $C_9H_{10}N_2S \cdot HCl$: C, 50.35; H, 5.16; N, 13.05. Found C, 50.50; H, 5.15; N, 13.07

EXAMPLE 2

4-[1-(3-Methylthien-2-yl)ethyl]-1H-Hydrochloride step A

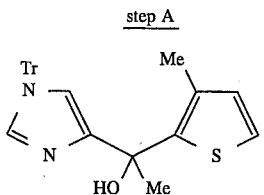

A2

A solution of methylmagnesium bromide (9.0 mL, 3.0M) was added to an ice-cooled solution of (3-methylthien-2-yl)-1-trityl-imidazol-4-yl methanone, B1, (10.1 g, 0.024 mol) in 25 mL of tetrahydrofuran was added. After 1 h, TLC analysis indicated that some unreacted starting material was present so additional methylmagnesium bromide (1.5 mL) was added. After 30 min of stirring, TLC analysis indicated that starting material was gone. The reaction was quenched with aqueous ammonium chloride solution and the resulting mixture was extracted with ethyl acetate. The ethyl acetate extracts were combined, washed with water and brine, dried ($Na_2SO_4$), and concentrated. The crude product was recrystallized from acetone to provide of the carbinol, A2, which was used directly in the next step.

step B

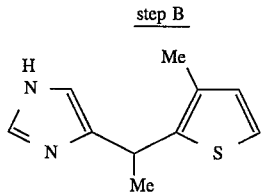

Cp-2

Over 2.5 h, a solution of $BH_3 \cdot THF$ (380 mL, 1.0M) in THF was added dropwise to a solution of TFA (86.8 g, 0.76 mol) in 75 mL of dry dichloromethane maintained below −10° C. during the addition. When the addition was complete, the reaction mixture was stirred for 10 min. Then a solution of the carbinol, A2, (8.6 g, 0.019 mol) in dry dichloromethane was added in one portion. The reaction mixture was stirred in ice for 90 minutes. The reaction was quenched by careful addition of 150 mL of 3N HCl. Then an equivalent volume of water was added. Most of the THF was evaporated in vacuo and then the mixture was basified with solid $Na_2CO_3$. This solution was extracted twice with ethyl acetate. The organic extracts were combined, washed with water, dried ($MgSO_4$), and concentrated. The residue was dissolved in 100 mL of methanol, and 3N HCl (25 mL) was added, and the mixture was refluxed for 2.5 h. The solution was allowed to cool overnight and then was concentrated in vacuo to give an amber syrup. This material was dissolved in water and extracted twice with diethyl ether, then it was basified and extracted with EtOAc. The organic extracts were dried ($K_2CO_3$) and filtered. The filtrate was treated with ethereal HCl solution, and the resulting precipitate (2.3 g) was collected. Additional ethereal HCl was added to the filtrate to provide a second crop of crystals which contained an impurity. These were recrystallized from acetone with filtration through Dicalite to provide purified material which was combined with the first crop. Recrystallization from acetone afforded 2.2 g of 4-[1-(3-methylthien-2-yl)ethyl]-1H-imidazole hydrochloride, Cp-2, as a white solid, mp 164°–166° C. The $^1$H NMR in DMSO-$d_6$ supported the assigned structure: d1.55–1.65 (d, 3H, Me), 2.15–2.25 (s, 3H, Me), 4.55–4.65 (q, 1H, CH), 6.85–6.90 (d, 1H), 7.30–7.35 (d, 1H), 7.40–7.50 (s, 1H), 9.05–9.10 (s 1H), 14.6–14.8 (br s, 2H). Elemental analysis: Calculated for $C_{10}H_{12}N_2S \cdot HCl$: C, 52.51; H, 5.73; N, 12.25. Found C, 52.56; H, 5.65; N, 12.27

EXAMPLE 3

4-[(3-Bromothien-2-yl)methyl]-1H-imidazole Hydrochloride step A

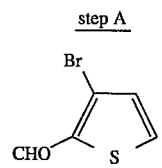

A3

To a solution of 2,3-dibromothiophene (24.2 g, 0.10 mol) in 200 mL of anhydrous diethyl ether cooled to −78° C. was added a solution of n-BuLi (66 mL, 1.6M) in hexanes. When addition was complete, the solution was stirred for 30 min. Then a −78° C. cooled solution of DMF (18.3 g, 0.25 mol) in 50 mL of anhydrous ether was added to the thiophene mixture via cannulation. When addition was complete, the reaction mixture was allowed to warm to ambient temperature and was left to stir overnight. The reaction was quenched with water, and the mixture was transferred to a separatory funnel. The layers were separated, and the aqueous layer was extracted with ether. The organic layers were combined, washed with water and brine, dried ($MgSO_4$), and concentrated to give an oil. Distillation through a Vigreux column provided 3-bromothiophene-2-carboxaldehyde, A3, as a yellow oil, bp 108°–109° C. The $^1$H NMR in DMSO-$d_6$ supported the assigned structure.

step B

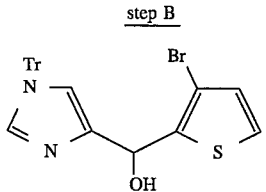

B3

To a solution of 4-iodo-1-trityl imidazole (10.9 g, 0.025 mol) in 75 mL of dry dichloromethane under nitrogen was added dropwise a solution of ethyl magnesium bromide in diethyl ether (3.0M, 8.5 mL). After 1 h, an additional 1.5 mL of Grignard was added to complete the exchange. The reaction mixture was stirred for 1 h at 25° C. TLC analysis indicated that the starting material was gone so 3-bromothiophene-2-carboxaldehyde, A3, (4.8 g, 0.025 mol) was added as a solution in 25 mL of dry dichloromethane. After overnight stirring at ambient temperature, the reaction was quenched with saturated ammonium chloride solution. The layers were separated, and the aqueous layer was extracted again with dichloromethane. The organic layers were combined, dried (Na$_2$SO$_4$), and concentrated. The residue was recrystallized from acetone to afford 8.4 g of (3-bromothieno-2-yl)-1-tritylimidazol-4-yl-methanol, B3, as a beige solid. A second crop was collected which was recrystallized twice from ethyl acetate to give an additional 0.4 g of product. The $^1$H NMR in CDCl$_3$ supported the assigned structure.

step C

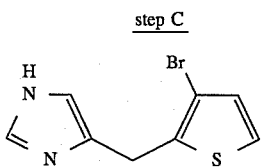

Cp-3

Over 2.5 h, a solution of BH$_3$•THF (90 mL, 1.0M) in THF was added dropwise over 45 min to a solution of TFA (18.2 g, 0.16 mol) in 25 mL of dry dichloromethane maintained at 10° C. during the addition. When the addition was complete, the reaction mixture was stirred for 15 min. Then a solution of the carbinol, B3, (2.0 g, 0.040 mol) in dry dichloromethane was added in one portion, and the reaction mixture was warmed to ambient temperature and stirred for 1 h. The reaction was quenched with water and then 3N HCl (20 mL) was added. Most of the THF was evaporated in vacuo and then the mixture was basified with solid Na$_2$CO$_3$. This solution was extracted twice with ethyl acetate. The organic extracts were combined, washed with water, dried (MgSO$_4$), and concentrated. The residue was dissolved in 100 mL of methanol, and 3N HCl (25 mL) was added, and the mixture was refluxed for 2.5 h. The solution was allowed to cool overnight and then was concentrated in vacuo to give an amber syrup. This material was dissolved in water and extracted twice with diethyl ether, then it was basified and extracted with EtOAc. The filtrate was treated with ethereal HCl solution, and the resulting precipitate was collected as a white solid. This material was recrystallized with filtration through Dicalite from acetonitrile with the addition of a little methanol. A second recrystallization was conducted to give 0.49 g of 4-[(3-bromothien-2-yl)methyl]-1H-imidazole, Cp-3, hydrochloride as a white solid, mp 211.5°–213.5° C. The $^1$H NMR in DMSO-d$_6$ supported the assigned structure: d4.25 (s, 2H), 7.10 (d, 1H), 7.45 (s, 1H), 7.60 (d, 1H), 9.00 (s, 2H). Elemental analysis: Calculated for C$_8$H$_7$BrN$_2$S•HCl: C, 34.37; H, 2.88; N, 10.02. Found C, 34.35; H, 2.86; N, 10.07

EXAMPLE 4

4-[1-(3-Bromothien-2-yl)-ethyl]-1H-imidazole Hydrochloride step A

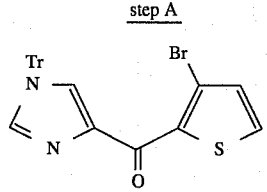

To a solution of (3-bromothien-2-yl)-1-tritylimidazol-4-yl-methanol, B3, (17.3 g, 0.0345 mol) in 300 mL of dichloromethane was added MnO$_2$ (17.2 g). TLC analysis indicated that the starting material was gone after 2 h. The reaction mixture was filtered, and the filtrate was concentrated to provide 4-(3-bromothiophen-2-yl)-1-trityl-imidazol-4-yl methanone, A4, which was used directly in the next step.

step B

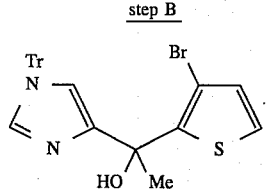

B4

A solution of methylmagnesium bromide (2.0 mL, 3.0M) in diethyl ether was added to a solution of 4-(3-bromothien-2-yl)-1-tritylimidazol-4-yl methanone, A4, (2.0 g, 0.0045 mol) in 40 mL of tetrahydrofuran. The reaction mixture was stirred for 1 h. The reaction was quenched with aqueous ammonium chloride solution, and the resulting mixture was extracted with ethyl acetate. The ethyl acetate extracts were combined, dried (Na$_2$SO$_4$), and concentrated to give a light yellow solid. The residue was recrystallized to give 1.75 g (84%) of 1-[(3-bromothien-2-yl)-1-trityl imidazol-4-yl]-ethanol, B4, as a white solid. The $^1$H NMR in CDCl$_3$ supported the assigned structure.

step C

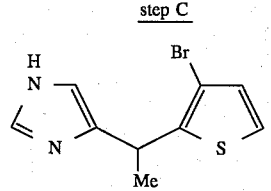

Cp-4

Over 2.5 h, a solution of BH$_3$•Me$_2$S (413 mL, 1.0M) in dichloromethane was added dropwise to a solution of TFA (62.8 g, 0.55 mol) in 200 mL of dry dichloromethane maintained at 0° C. After the addition was completed the mixture was stirred an additional 2 h, then a solution of the 1-[(3-bromothien-2-yl)-1-trityl imidazol-4-yl]-ethanol, B4, (7.1 g, 0.014 mol) in dry dichloromethane was added in one portion and the reaction mixture was warmed to ambient temperature overnight. The reaction was quenched by addition of 250 mL of MeOH/3N HCl (4:1) and the mixture was refluxed for 2 hrs. After cooling to room temperature most of the MeOH was evaporated in vacuo, then the mixture was diluted with water and washed twice with Et$_2$O. Aqueous layer was basified with Na$_2$CO$_3$ and extracted with EtOAc. The extracts were combined, dried (K$_2$CO$_3$) and filtered. The solvent was evaporated in vacuo to give a light yellow syrup which was purified on flash silica gel with 98.1:1 EtOAc/MeOH/NH₄OH to afford 3.2 g of free base which was converted to its HCl salt. This material was recrystallized from acetonitrile to provide 2.6 g of the target, Cp-4, as a light yellow solid, mp 184°–188° C. The ¹H NMR in DMSO-d₆ supported the assigned structure: d1.65 (d, J=7.1 Hz, 3H, Me), 4.60 (q, 1H, CH), 7.10 (d, J=5.3 Hz, 1H), 7.60 (s, 1H), 7.68 (d, 1H), 9.10 (s, 1H), 14.50 (br s, 1H). Elemental analysis: Calculated for $C_9H_9BrN_2S \cdot HCl$: C, 36.82; H, 3.43; N, 9.54. Found C, 36.98; H, 3.29; N, 9.62.

EXAMPLE 5

4-[-(3,4-Dimethylthien-2-yl)methyl]-1H-imidazole Fumarate step A

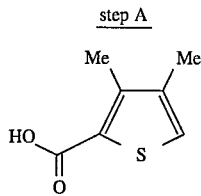

A5

To a solution of ethyl 3,4-dimethylthiophene-2-carboxylate (Wynberg, H.; Zwanenburg, D. J. *J. Org. Chem.* 1964, 29, 1919; Chadwick, D. J.; Chambers, J.; Meakins, G. D.; Snowden, R. L. *J. Chem. Soc. Perkin Trans. 1* 1972, 2079) (12.36 g, 0.0671 mol) in 15 mL of ethanol and 5 mL of water was added KOH (5.64 g, 0.1 mol). The solution was swirled on a steam bath until the reaction mixture became homogeneous. The reaction was heated for 1.5 h, cooled and acidified with 6N HCl. The suspension was filtered to give 10.97 g (quantitative yield) of 3,4-dimethylthiophene-2-carboxylate, A5, which was taken on directly in the next step.

step B

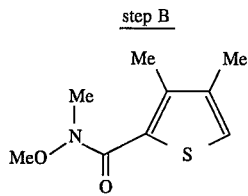

B5

To a solution of 3,4-dimethylthiophene-2-carboxylic acid, A5, (21.3 g, 0.070 mol) in 50 mL was added thionyl chloride. The reaction mixture was refluxed overnight and then was allowed to cool. In a separate flask, a solution of N,O-dimethylhydroxylamine hydrochloride (8.7 g, 0.089 mol) and triethylamine (10.1 g, 0.1 mol) in 100 mL of chloroform was cooled in ice. Then the solution of 3,4-dimethylthiophene-2-carboxylic acid chloride was added. The reaction mixture was allowed to warm to ambient temperature and was stirred 2 h. The reaction mixture was poured into a separatory funnel and washed with dilute aqueous hydrochloric acid, water, dilute sodium hydroxide, and then water. The organic layer was dried (MgSO₄) and concentrated. By TLC, some 3,4-dimethylthiophene-2-carboxylic acid was present so the crude product was dissolved in diethyl ether, and this solution was washed with 3N NaOH, water, and brine and then was dried (MgSO₄) and concentrated. The crude product was distilled under vacuum to provide 6.4 g (52%) of N,O-dimethyl-3,4-dimethylthiophene-2-carboxamide, B5, as a clear liquid, bp 85°–86° C. (0.1 mmHg). The ¹H NMR in CDCl₃ supported the assigned structure.

step C

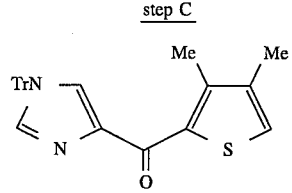

C5

To a solution of 4-iodo-1-trityl imidazole (10.5 g, 0.024 mol) in 100 mL of dry dichloromethane under nitrogen was added dropwise a solution of ethyl magnesium bromide (8.0 mL, 3.0M) in diethyl ether. When addition was complete, the reaction mixture was stirred for 1 h at 25° C. TLC analysis indicated that the starting material was gone so N,O-dimethyl-3,4-dimethylthiophene-2-carboxamide, B5, (4.78 g, 0.024 mol) was added as a solution in dichloromethane. After overnight stirring at ambient temperature, the reaction was quenched with saturated ammonium chloride solution. The layers were separated, and the aqueous layer was extracted again with dichloromethane. The organic layers were combined, dried (Na₂SO₄), and concentrated. Diethyl ether was added to the residue, and the solution was cooled in ice. A white solid came out of solution. Filtration afforded 8.2 g of (3,4-dimethylthien-2-yl)-1-trityl-imidazol-4-yl methanone, C5, as a white solid. The ¹H NMR in CDCl₃ supported the assigned structure.

step D

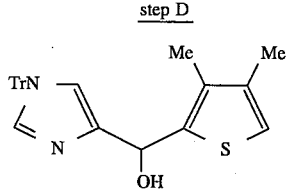

D5

A solution of (3,4-dimethylthien-2-yl)-1-trityl-imidazol-4-yl methanone, C5, (3.4 g, 0.0075 mol) and sodium borohydride in 50 mL of 2-propanol was heated at reflux for 2 h. After cooling, 3N hydrochloric acid solution was added to the reaction mixture followed by 10% aqueous sodium carbonate solution. The mixture was concentrated under reduced pressure and the resulting solution was extracted twice with chloroform. The chloroform extracts were combined, dried (Na₂SO₄), and concentrated. The residue was recrystallized from ethyl acetate with a small amount of chloroform to give a white solid. The mother liquor was concentrated to give a second crop of the desired (3,4-dimethylthien-2-yl)-1-trityl-imidazol-4-yl-methanol, D5. The ¹H NMR in CDCl₃ supported the assigned structure.

step E

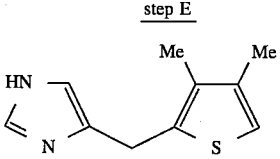

Cp-5

A solution of (3,4-dimethylthien-2-yl)-1-trityl-imidazol-4-yl-methanol, D5, in 50 mL of ethanol containing 1N hydrochloric acid (4.0 mL) and palladium hydroxide (1.0 g) was shaken with hydrogen at 60 psi at 50° C. on a Parr hydrogenator for 40 h. The solution was cooled and filtered to remove the catalyst. The filtrate was concentrated under reduced pressure. The residue was diluted with water and extracted twice with diethyl ether, and then was basified with Na₂CO₃ This solution was extracted twice with ethyl acetate. The organic layers were combined, dried (K₂CO₃), and concentrated. The residue was dissolved in diethyl ether and ethereal hydrogen chloride was added. A precipitate formed which was collected by suction filtration and then recrystallized from acetonitrile to provide 0.21 g of 4-[(3,4-dimethylthien-2-yl)methyl]-1H-imidazole hydrochloride, Cp-5, as a white solid, mp 180°–182° C. The ¹H NMR in DMSO-d₆ supported the assigned structure: d2.00 (s, 3H, Me), 2.20 (s 3H, Me), 4.15 (s, 2H, CH₂), 6.95 (s, 1H), 7.40 (s, 1H), 9.00 (s, 1H), 14.42 (br s, 2H). Elemental analysis: Calculated for $C_{10}H_{12}N_2S \cdot HCl$: C, 52.51; H, 5.72; N, 12.25. Found C, 52.54; H, 5.79; N, 12.28.

EXAMPLE 6

4-[-(3,4-Dimethylthien-2-yl)ethyl]-1H-imidazole Fumarate step A

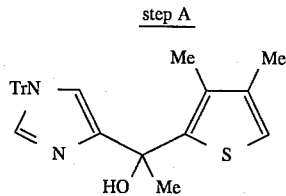

A6

To a solution of (3,4-dimethylthien-2-yl)-1-trityl-imidazol-4-yl methanone, C5, (2.0 g, 0.0045 mol) in 20 mL of tetrahydrofuran was added a solution of methylmagnesium bromide (1.5 mL, 3.0M). The reaction mixture was stirred overnight at ambient temperature. The reaction was quenched with aqueous ammonium chloride solution and the resulting mixture was extracted with ethyl acetate. The organic extracts were combined, dried ($Na_2SO_4$), and concentrated. The residue was recrystallized to give 1.75 g (84%) of the desired carbinol, A6, as a white solid. The ¹H NMR in $CDCl_3$ supported the assigned structure.

step B

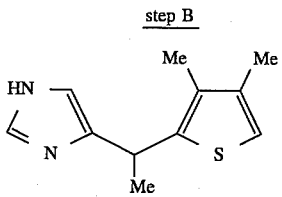

Cp-6

A solution of the above carbinol, A6, in 50 mL of ethanol containing 1N hydrochloric acid (3.8 mL) and palladium hydroxide (0.9 g) was shaken with hydrogen at 60 psi at 50° C. on a Parr hydrogenator for 24 h. After cooling, the solution was filtered to remove the catalyst, and the filtrate was concentrated in vacuo. The residue was diluted with water and extracted twice with diethyl ether, and then basified with $Na_2CO_3$. This solution was extracted twice with ethyl acetate. The organic layers were combined, dried ($K_2CO_3$), and concentrated. The residue was absorbed onto a flash silica gel column (5 g) which was eluted with 97.5:2.5 chloroform:10% $NH_4OH$ in methanol. The product containing fractions were combined and concentrated to give 0.46 g (59%) of the desired product as free base. A solution of this material in 2-propanol was heated with fumaric acid (260 mg). The solvent was evaporated and the residue was recrystallized from acetone to provide 0.36 g of a white solid, Cp-6, mp 127°–129° C. The ¹H NMR in DMSO-d₆ supported the assigned structure: d1.65 (d, J=7.1 Hz, 3H, Me), 2.00 (s, 3H, Me), 2.10 (s, 3H, Me), 4.37 (q, 1H, CH), 6.65 (s, 2H, fumaric acid), 6.77 (s, 1H), 6.87 (s, 1H), 7.55 (s, 1H). Elemental analysis: Calculated for $C_{11}H_{14}N_2S \cdot C_4H_4O_4$: C, 55.89; H, 5.63; N, 8.69. Found C, 55.99; H, 5.74; N, 8.38.

EXAMPLE 7

4-[-(3,4-Dibromothien-2-yl)methyl]-1H-imidazole Fumarate step A

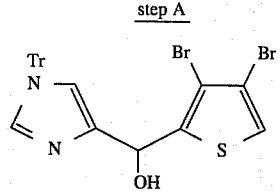

A7

A solution of 2,3,4-tribromothiophene (2.46 g, 0.0076 mol) in 20 mL of tetrahydrofuran was cooled to –78° C. and then a precooled (78° C.) solution of n-butyllithium (4.75 mL, 2.5M) in hexanes was added by cannulation. This solution was stirred for 20 min, and then a solution of 1-trityl-imidazole-4-carboxaldehyde (4.4 g, 0.76 mol) in 100 mL of THF was added by cannula. When the addition was complete, the reaction mixture was allowed to warm to ambient temperature overnight. The reaction was quenched with aqueous ammonium hydroxide and extracted with ethyl acetate to give a brown semisolid. This material was chromatographed on flash silica gel using 1% methanol-chloroform as eluent. The fractions which contained impure product were combined and concentrated and the residue recrystallized from ethyl acetate. The recrystallization was not successful so the collected solid and mother liquor were combined and chromatographed on flash silica as before. The fractions containing pure product were concentrated and combined with the pure product obtained from the previous column. These were combined and recrystallized from ethyl acetate to give the desired carbinol, A7, as a white solid which was taken on directly in the next step.

step B

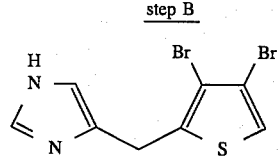

Cp-7

A solution of $BH_3 \cdot Me_2S$ (44 mL, 1.0M) in dichloromethane was added dropwise to a solution of TFA (6.5 g, 0.152 mol) in 25 mL of dry dichloromethane at 0° C. When the addition was complete, the reaction mixture was stirred for 90 min. Then the carbinol, A7, (0.84 g, 0.00144 mol) was added in one portion and the reaction mixture was warmed to ambient temperature and stirred overnight. The reaction was quenched with 75 mL of 3N HCl which was cautiously added at first. Then the mixture was refluxed on a steam bath for 2 h. The solution was cooled and then concentrated in vacuo to provide a brown oil. The residue was dissolved in water. This solution was washed twice with ether, basified with $Na_2CO_3$ and extracted with ethyl acetate. The ethyl acetate extracts were combined, dried ($Na_2SO_4$), and concentrated. The residue was dissolved in ether, filtered to remove a small amount of insolubles and treated with 1.0 equivalent of ethereal HCl. A white solid was collected which was recrystallized from acetonitrile with a small amount of methanol with filtration through Dicalite to provide 0.35 g of 4-[-(3,4-dibromothien-2-yl)methyl]-1H-imidazole fumarate, Cp-7, as a white solid, mp 224°–227° C.

The $^1$H NMR in DMSO-$d_6$ supported the assigned structure: d4.30 (s, 2H, CH$_2$), 7.50 (s, 1H), 7.90 (s, 1H), 9.05 (s, 1H). Elemental analysis: Calculated for C$_8$H$_6$N$_2$S•HCl: C, 26.80; H, 1.97; N, 7.81. Found C, 26.86; H, 1.96; N, 7.79.

EXAMPLE 8

4-[-(3,4-Dibromothien-2-yl)ethyl]-1H Fumarate step A

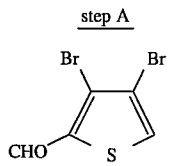

A solution of 2,3,4-tribromothiophene (2.56 g, 0.0080 mol) in 20 mL of diethyl ether was cooled to −78° C. and then n-butyllithium (5.0 mL, 1.6M) in hexanes was added slowly from an addition funnel. When the addition was complete, the reaction mixture was stirred for 15 minutes. Then DMF (0.88 g, 1.2 mol) was added in one portion. The reaction mixture was gradually warmed to room temperature and was left to stir overnight. The reaction was quenched with aqueous ammonium chloride solution and extracted twice with diethyl ether. The organic extracts were combined, washed with two small portions of water and then brine and dried (MgSO$_4$). The solution was filtered and concentrated, and the residue was purified on flash silica gel with 2.5% diethyl ether-hexanes to provide 1.1 g of 3,4-dibromothiophene-2-carboxaldehyde as an off-white solid. The above sequence was repeated as above except that the n-butyllithium was cooled to −78° C. and then was added to the thiophene solution by cannulation. The reaction mixture was stirred for 2 h before DMF was added. The reaction was worked up as before and the crude product was recrystallized from ether to give 0.9 g of product. A third preparation was also done. A solution of 2,3,4-tribromothiophene (4.8 g, 0.015 mol) in 20 mL of diethyl ether was cooled to −78° C. and then n-butyllithium (10.0 mL, 1.6M) was added slowly from an addition funnel. When the addition was complete, the reaction mixture was stirred for 15 minutes. Then DMF (1.82 g, 0.025 mol) was added in one portion. The reaction mixture was gradually warmed to room temperature, and was left to stir overnight. The reaction was quenched with aqueous ammonium chloride solution and extracted twice with diethyl ether. The organic extracts were combined, washed with two small portions of water and then brine and dried (MgSO$_4$). The solution was filtered and concentrated, and the residue was purified on flash silica gel with 2.5% diethyl ether-hexanes. The product was combined with the previous batches of 3,4-dibromothiophene-2-carboxaldehyde and recrystallized from diethylether to give 3.7 g of 3,4-dibromothiophene-2-carboxaldehyde, A8, whose NMR in CDCl$_3$ supported the desired product structure.

step B

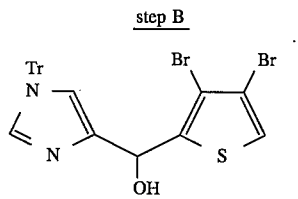

To a solution of 4-iodo-1-trityl imidazole (5.8 g, 0.0133 mol) in 75 mL of dry dichloromethane under nitrogen was added dropwise a solution of ethyl magnesium bromide in diethyl ether (4.4 mL, 3.0M). When addition was complete, the reaction mixture was stirred for 45 min at 25° C. TLC analysis indicated that some starting material remained so an additional 1.0 mL of Grignard reagent was added. After 1 h of stirring, TLC analysis indicated that the starting material was gone, and 3,4-dibromothiophene-2-carboxaldehyde, A8, (3.6 g, 0.0133 mol) was added as a solution in dichloromethane. After overnight stirring at ambient temperature, the reaction was quenched with saturated ammonium chloride solution. The layers were separated, and the aqueous layer was extracted again with dichloromethane. The organic layers were combined, dried (Na$_2$SO$_4$), and concentrated to provide an off-white solid. This material was recrystallized from ethyl acetate with a small amount of chloroform added to aid in dissolution. Filtration afforded 5.3 g (69%) of 4-(3,4-dibromothien-2-yl)methanol-1-trityl-imidazole, B8, as a white solid. The $^1$H NMR in CDCl$_3$ supported the assigned structure.

step C

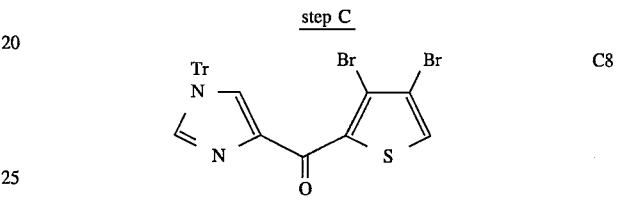

To a solution of the carbinol, B8, (3.5 g, 0.006 mol) in 100 mL of dichloromethane was added MnO$_2$ (2.0 g, 0.0230 mol). TLC analysis indicated that the starting material was gone after 2 h. The reaction mixture was filtered, and the filtrate was concentrated to provide (3,4-dibromothien-2-yl)-1-trityl-imidazol-4-yl methanone, C8, which was used directly in the next step.

step D

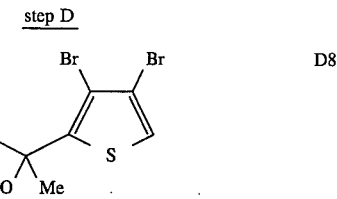

A solution of methylmagnesium bromide (0.55 mL, 3.0M) in diethyl ether was added to an ice-cooled solution of (3,4-dibromothien-2-yl)-1-trityl-imidazol-4-yl methanone, C8, (0.88 g, 0.0015 mol) in 20 mL of THF. After 30 min of stirring, the reaction was quenched with aqueous ammonium chloride solution, and the resulting mixture was extracted twice with ethyl acetate. The ethyl acetate extracts were combined, washed with water and brine, dried (Na$_2$SO$_4$), filtered, and concentrated. The crude product was recrystallized from diethyl ether to provide the carbinol, D8, as a buff-colored solid which was used directly in the next step.

step E

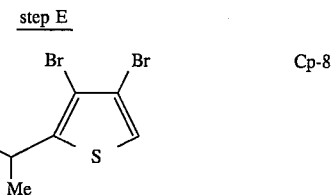

A solution of BH$_3$•Me$_2$S (30 mL, 1.0M) in dichloromethane was added dropwise to a solution of TFA (4.56 g, 0.040 mol) in 20 mL of dry dichloromethane at 0° C. When the addition was complete, the reaction mixture was stirred for 60 min. Then the carbinol, D8, (0.60 g, 0.0010 mol) was added in one portion. After 2 h of stirring, the reaction mixture was warmed to ambient temperature and stirred overnight. The reaction was quenched with 50 mL of 4:1 MeOH:3N HCl, and the resulting mixture was refluxed for 2 h. The solution was cooled and then concentrated in vacuo. The residue was dissolved in water and was washed twice with ether, basified with $Na_2CO_3$ and extracted twice with ethyl acetate. The ethyl acetate extracts were combined, dried ($K_2CO_3$), and concentrated. The residue was purified three times on flash silica gel with 99:0.5:0.5 ethyl acetate::methanol:ammonia to provide 100 mg of free base which was combined with fumaric acid (0.32 mg) in acetone-methanol. This solution was concentrated in vacuo, and the residue was triturated with ether. Filtration provided 4-[(3, 4-dibromothien-2-yl)ethyl]-1H-imidazole fumarate, Cp-8, as 0.066 g of a white solid, mp 128°–130° C. The $^1$H NMR in DMSO-$d_6$ supported the assigned structure: d1.60 (d, 3H, Me), 4.42 (q, 1H CH), 6.60 (s, 2H, fumaric acid), 7.02 (s, 1H), 7.60 (s, 1H), 7.75 (s, 1H). Elemental analysis: Calculated for $C_9H_8Br_2N_2S \cdot C_4H_4O_4$: C, 34.54; H, 2.68; N, 6.20. Found C, 35.08; H, 2.74; N, 6.20.

EXAMPLE 9

4-[-(4-Bromothien-2-yl)methyl]1H-imidazole Hydrochloride step A

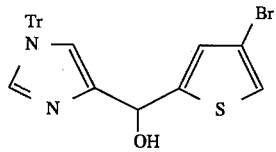

To a solution of 4-iodo-1-trityl imidazole (4.36 g, 0.010 mol) in 20 mL of dry dichloromethane under nitrogen was added dropwise a solution of ethyl magnesium bromide in THF (3.5 mL, 3.0M). When addition was complete, the reaction mixture was stirred for 45 min at 25° C. TLC analysis indicated that no starting material remained so 4-bromothiophene-2-carboxaldehyde (1.9 g, 0.010 mol) was added as a solution in dichloromethane. After overnight stirring at ambient temperature, the reaction was quenched with saturated ammonium chloride solution. The layers were separated, and the aqueous layer was extracted again with dichloromethane. The organic layers were combined, dried ($Na_2SO_4$), and concentrated to provide an off-white solid. This material was triturated with diethyl ether. Filtration afforded 4-(4-bromothien-2-yl)methanol-1-tritylimidazole, A9, as a white solid. The $^1$H NMR in CDCl$_3$ supported the assigned structure.

step B

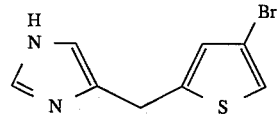

A solution of $BH_3 \cdot Me_2S$ (50 mL, 1.0M) in dichloromethane was added dropwise to a solution of TFA (9.1 g, 0.080 mol) in 25 mL of dry dichloromethane at 0° C. When the addition was complete, the reaction mixture was stirred for 60 min. Then the carbinol, A9, (1.0 g, 2.0 mmol) was added in one portion. After 2 h of stirring, the reaction mixture was warmed to ambient temperature for 1 h. The reaction was quenched with MeOH, followed by the addition of 20 mL of 3N HCl. The solution was basified with $Na_2CO_3$ and extracted twice with dichloromethane. The organic layers were combined, dried ($Na_2SO_4$), filtered and concentrated. The residue was triturated with ether. The ether extracts were treated with charcoal, filtered through Dicalite and then treated with $Et_2O \cdot HCl$ to give a white solid which was recrystallized from MeOH:MeCN to give the title compound, Cp-9, mp 186°–189.5° C. The $^1$H NMR in DMSO-$d_6$ supported the assigned structure: d 4.30 (s, 2H), 7.53 (s, 1H), 7.58 (s, 1H), 9.05 (s, 1H) 14.75 (br s, 1H). Elemental Anal. Calc for $C_8H_9BrN_2S \cdot HCl$ C, 34.37; H, 2.88: N, 10.02. Found C, 34.88; H, 2.75; N, 9.93.

What is claimed is:

1. A compound of the formulae:

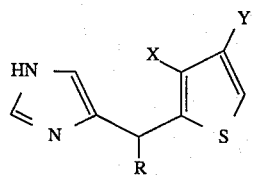

wherein

R is hydrogen or methyl,

X is hydrogen, $C_{1-4}$alkyl, bromine or chlorine, and

Y is hydrogen, $C_{1-4}$alkyl, bromine or chlorine;

with the proviso that X and Y are not both simultaneously hydrogen.

2. The compound of claim 1 selected from the group consisting of:

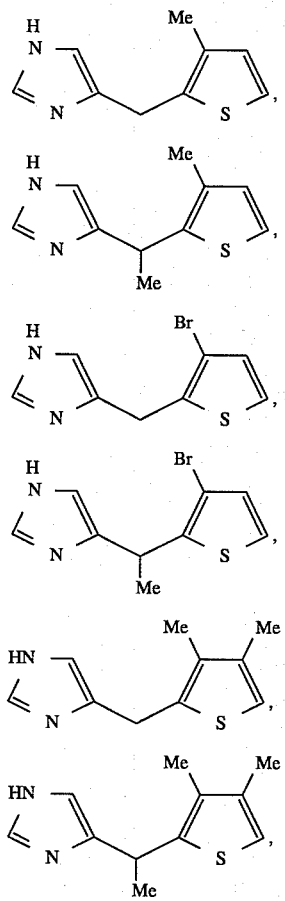

23
-continued
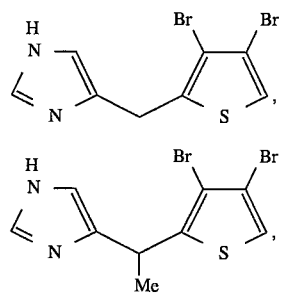
24
-continued
and
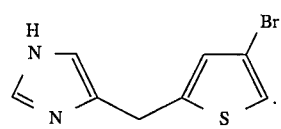
* * * * *